United States Patent
Höhne et al.

(10) Patent No.: US 10,222,331 B2
(45) Date of Patent: Mar. 5, 2019

(54) SENSOR CAP FOR OPTOCHEMICAL SENSOR

(71) Applicant: Endress+Hauser Conducta GmbH+Co. KG, Gerlingen (DE)

(72) Inventors: Thomas Höhne, Chemnitz (DE); Christian Fanselow, Geringswalde (DE); Andreas Löbbert, Waldheim (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 147 days.

(21) Appl. No.: 15/386,335

(22) Filed: Dec. 21, 2016

(65) Prior Publication Data
US 2017/0184499 A1    Jun. 29, 2017

(30) Foreign Application Priority Data

Dec. 23, 2015 (DE) .......... 10 2015 122 662
Mar. 2, 2016 (DE) .......... 10 2016 103 750

(51) Int. Cl.
*H01J 40/14* (2006.01)
*G01N 21/64* (2006.01)
(Continued)

(52) U.S. Cl.
CPC .......... *G01N 21/645* (2013.01); *G01N 21/03* (2013.01); *G01N 21/643* (2013.01);
(Continued)

(58) Field of Classification Search
CPC .... G01N 21/03; G01N 21/643; G01N 21/645; G01N 21/7703
(Continued)

(56) References Cited

U.S. PATENT DOCUMENTS 3,928,161 A    12/1975   McIntyre et al.
4,903,481 A    2/1990    Schuster et al.
(Continued)

FOREIGN PATENT DOCUMENTS

AT    391030 B       8/1990
DE    3211533 A1    12/1982
(Continued)

*Primary Examiner* — Kevin Pyo
(74) *Attorney, Agent, or Firm* — Kelly J. Smith; PatServe (57) ABSTRACT

The present disclosure relates to a sensor cap for an optochemical sensor for determining or monitoring at least one analyte present in a medium having a substantially cylindrical plug-in component and a sleeve-shaped outer component. The plug-in component has an optical component with a convex-shaped surface region for optimal flow, and the optical component at least partially consists of a material transparent to measuring radiation. On the surface region of the optical component is an analyte-sensitive matrix having at least one functional layer. The plug-in component and the sleeve-shaped component are designed such that the connecting region coming into contact with the medium is between the plug-in component and the sleeve-shaped outer component in the edge region of the optical component or is at a radial distance from the edge region of the optical component, and is sealed, without a gap, facing the medium.

18 Claims, 6 Drawing Sheets

(51) Int. Cl.
*G01N 21/03* (2006.01)
*G01N 21/77* (2006.01)
(52) U.S. Cl.
CPC . *G01N 21/7703* (2013.01); *G01N 2021/0321* (2013.01); *G01N 2021/0385* (2013.01); *G01N 2021/6434* (2013.01); *G01N 2021/6439* (2013.01); *G01N 2021/6463* (2013.01); *G01N 2021/6484* (2013.01); *G01N 2021/772* (2013.01); *G01N 2021/775* (2013.01); *G01N 2021/7786* (2013.01)
(58) Field of Classification Search
USPC .................. 250/226; 73/23.2, 23.31, 23.32
See application file for complete search history.

(56) References Cited

U.S. PATENT DOCUMENTS

| | | | |
|---|---|---|---|
| 7,087,151 B2 * | 8/2006 | Mizutani | G01N 27/4074 204/429 |
| 2010/0203649 A1 * | 8/2010 | Thrier | G01N 31/225 436/127 |

FOREIGN PATENT DOCUMENTS

| | | |
|---|---|---|
| DE | 3323241 A1 | 1/1985 |
| DE | 3889757 T2 | 12/1994 |
| DE | 102005033926 A1 | 1/2007 |
| DE | 102008007317 A1 | 8/2009 |
| EP | 0039380 A2 | 11/1981 |
| EP | 0126600 B1 | 11/1984 |

\* cited by examiner

Prior Art

SENSOR CAP FOR OPTOCHEMICAL SENSOR

CROSS-REFERENCE TO RELATED APPLICATIONS

The present application is related to and claims the priority benefit of German Patent Application Nos. 10 2015 122 662.6, filed on Dec. 23, 2015 and 10 2016 103 750.8, filed on Mar. 2, 2016, the entire contents of which are incorporated herein by reference.

TECHNICAL FIELD

The present disclosure relates to a sensor cap for an optochemical sensor for determining or monitoring at least one analyte present in a medium, as well as an electrochemical sensor equipped with the sensor cap according to the present disclosure.

BACKGROUND

An optochemical analyte sensor such as an oxygen sensor is based upon the principle of analyte-induced fluorescence or luminescence quenching of an organic dye, which is normally introduced into a polymer matrix. In particular, the polymer/dye mixture tailored for a given analyte is applied as a solid film to a substrate such as a glass plate or an optical waveguide.

A device was disclosed in WO 2005/100 957 A1 for determining and/or monitoring an analyte contained in a fluid process medium. The known device has a sensor with a measuring membrane, which possesses a porous support structure. A luminescent substance is embedded in the support structure and comes into contact with the process medium. Furthermore, a transmitting unit and a receiving unit are provided, wherein the transmitting unit transmits measuring radiation, and the luminescent substance is excited to emit luminescent radiation, and wherein the receiving unit detects the correspondingly generated luminescent radiation. A control/evaluation unit detects a concentration or partial pressure/pressure of the analyte in the process medium based upon the quenching of the luminescent radiation of the luminous substance. Luminescence is, incidentally, the generic term for the generation of optical radiation in a substance that occurs with the transition from an excited state to the basic state.

Figures 1, 1A:
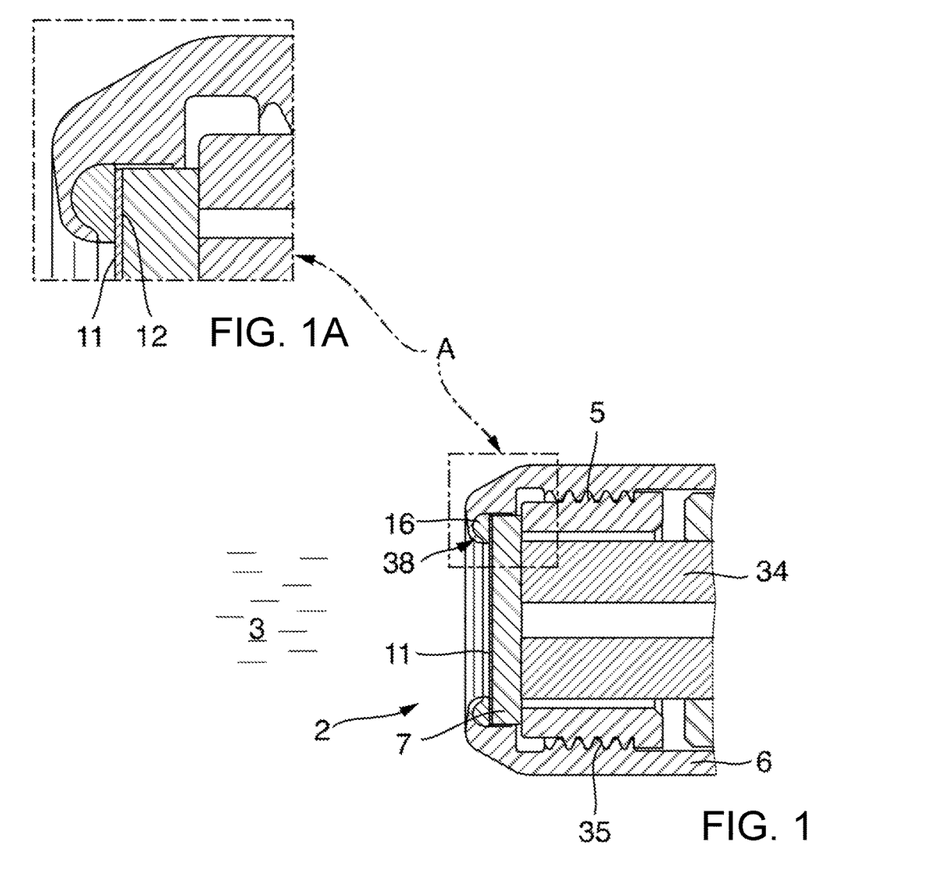
FIG. 1 shows a longitudinal section of a sensor cap known from the prior art.
FIG. 1A shows an enlargement of the section designated A from FIG. 1.

An oxygen sensor which is offered and marketed by the applicant is shown in FIG. 1 of the following description of figures. Given the gap-free seal between the sensor housing and sensor membrane, this sensor satisfies the demanding hygienic requirements placed upon sensors when they are used in, for example, the food industry. If the known oxygen sensor is, however, in a pipeline through which a medium containing an analyte flows, bubble formation can occur on the surface of the membrane facing the medium. Of course, due to the formation of bubbles on the surface of the membrane, the measured values for oxygen, as the analyte to be determined in the flowing medium, are significantly distorted.

A sensor cap was disclosed in DE 10 2011 088 012 A1 that has a convex shape facing the medium. The sensing element is fastened to a convex-shaped surface facing the medium. Neither the advantage of this convex shape nor the satisfaction of hygienic requirements is addressed in this patent application.

SUMMARY

The object of this disclosure is a flow-optimized sensor cap and a corresponding sensor for use in hygienic applications.

The object is achieved by a sensor cap for an optochemical sensor for determining or monitoring at least one analyte present in a medium and having a substantially cylindrical plug-in component and a sleeve-shaped outer component. In the end region facing the medium, the plug-in component has an optical component with a surface region that is shaped for optimal flow. The surface region is preferably convex-shaped. In the area of the surface region, the optical component at least partially consists of a material transparent to measuring radiation. Provided on the convex-shaped surface region of the optical component is a matrix that has at least one analyte-sensitive functional layer with a substance sensitive to the analyte. The plug-in component and the sleeve-shaped component are designed such that the connecting region coming into contact with the medium is between the plug-in component and the sleeve-shaped outer component in the edge region of the convex-shaped surface region of the optical component or is at a radial distance from the edge region of the convex-shaped surface region of the optical component, and is sealed, without a gap, facing the medium.

The analytes to be determined or monitored are any ions or gases, such as oxygen, chlorine, etc., that are present in the medium. The matrix with the analyte-sensitive functional layer preferably consists of several functional layers. In several embodiments of the present disclosure, the matrix, or at least one of the functional layers of the matrix, can be arranged in or on a substrate film consisting of plastic or a metal mesh. This combination of a matrix with at least one functional layer and carrier medium is termed a membrane in the present disclosure. The examples, which do not restrict the present disclosure, are described below.

The sensor cap according to the present disclosure has, inter alia, the following advantages:

The bubble adhesion to the analyte-sensitive matrix or membrane is prevented by the flow-optimized surface region.

The design of the sensor cap satisfies demanding hygienic requirements that are very important, particularly in the food industry.

The design of the sensor cap is stress-resistant.

According to an embodiment of the sensor cap according to the present disclosure, the sensitive matrix, as mentioned above, is a multilayer system that consists of at least two functional layers, wherein one of the functional layers includes the analyte-sensitive substance. Known sensors frequently have three functional layers, such as a first functional layer that is selectively permeable to the analytes, a second functional layer for chemical and/or mechanical stability, and a third functional layer that includes the analyte-sensitive, and thus sensor-specific, substance. When correspondingly excited by a light source, this third functional layer transmits a luminescence or fluorescence or phosphorescence signal at a specific wavelength and/or an analyte-specific phase angle, or it absorbs specific wavelengths of the radiated light. The corresponding change in the measuring radiation is detected and is a measure of the concentration of the analyte in the medium.

Figure 4:
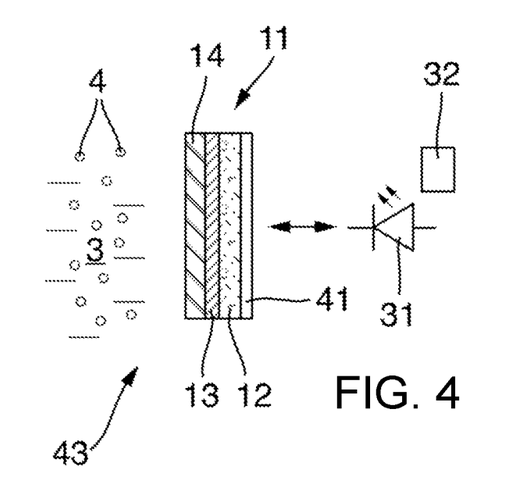
FIG. 4 shows a cross-section of a first variant of an analyte-sensitive membrane, which is used together with the sensor cap according to the present disclosure.
Figure 6:
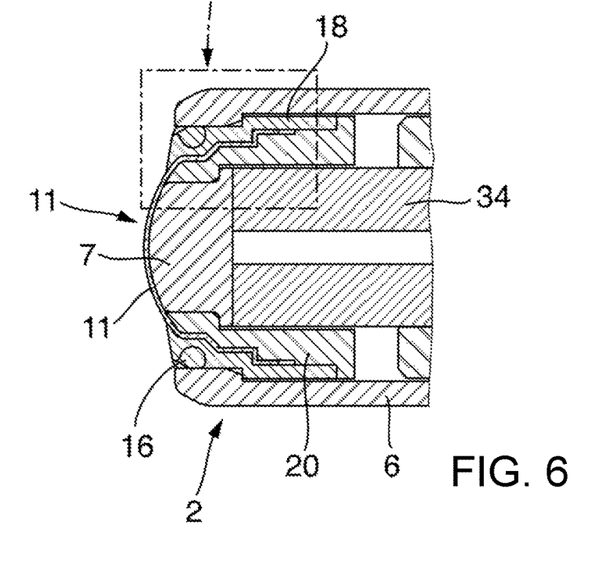
FIG. 6 shows a longitudinal section of a third variant of the sensor cap according to the present disclosure.

The membrane must be a membrane through which the analyte can diffuse. It is, however, also possible for a membrane to have a transparent, non-diffusible substrate film. This blocks the analyte. Two corresponding membrane designs are shown in FIG. 4 and FIG. 6.

In one embodiment of the sensor cap according to the present disclosure, the analyte-sensitive matrix is arranged on or in a membrane through which the analyte can diffuse, which is connected to the convex-shaped surface region. The connection between the surface region and membrane or matrix is designed to be either separable or inseparable. If the membrane consists of several functional layers, the connection between the individual functional layers must be designed such that it is chemically and physically inert, even at high temperatures and pressures.

According to an embodiment of the sensor cap according to present disclosure, the plug-in component is designed as a single piece. The analyte-sensitive matrix and/or the membrane is/are designed to be flexible and, additionally, serve as a means of sealing for the gap-free seal between the plug-in component and sleeve-shaped outer component.

In a first variant of the sensor cap according to present disclosure, the plug-in component is also designed as a single piece. An annular recess for receiving a sealing ring is provided in the edge region of the convex-shaped surface region. The recess and sealing ring are positioned and designed so that the connecting region that comes into contact with the medium and is between the plug-in component and sleeve-shaped outer component is sealed gap-free against the medium.

In a second variant of the sensor cap according to the present disclosure, the plug-in component in the axial overlapping region with the sleeve-shaped outer component consists of two components: an outer ring with a stepped inner contour, and an inner ring with an outer contour corresponding to the inner contour. The optical component is connected to the inner ring in the edge region of the convex-shaped surface region.

In the above-described second variant of the sensor cap according to the present disclosure, the membrane with the sensitive matrix is dimensioned to be larger than the convex-shaped surface region of the optical component. The edge region of the membrane projecting beyond the convex-shaped surface region is affixed between the inner ring and outer ring of the plug-in component. Fixation preferably occurs by means of pressing the outer ring and inner ring.

According to a modification of the second variant of the sensor cap according to the present disclosure, the inner ring with the outer contour is an integral part of the plug-in component.

In another embodiment, there is an annular recess for accommodating a sealing ring in the edge region of the outer ring facing the medium. The recess and sealing ring are positioned and designed so that the connecting region that comes into contact with the medium and is between the outer ring of the plug-in component and sleeve-shaped outer component is sealed gap-free against the medium.

In conjunction with the above-described sensor cap, the inner edge of the outer ring facing toward the convex-shaped surface region is designed such that it forms a gap-free, annular contact region with the flexible, sensitive matrix or the sensitive matrix designed as a flexible membrane. Accordingly, the membrane or the matrix additionally takes on the sealing of the inner chamber of the sensor cap for the process. Since this seal is gap-free, it satisfies the demanding hygienic requirements imposed upon sensors in some fields of automation engineering.

It has already been mentioned above that the individual components of the sensor cap are connected by means of pressing. Alternatively, the inner contour of the outer ring and the outer contour of the inner ring have a corresponding helical thread and are screwed together. In this embodiment the outer ring and inner ring can be connected to each other using a specific torque.

To specifically limit the position of the plug-in component and the sleeve-shaped outer component in an axial direction, stop edges are provided on the inner surface of the sleeve-shaped outer component and the outer surface of the plug-in component.

The object of this disclosure is further achieved by an optochemical sensor for determining or monitoring at least one analyte present in a medium. This comprises a sensor cap according to the present disclosure, as described above in various embodiments, an electronics component with a light source, a detection unit, and a control/evaluation unit.

In an embodiment, the optical component is designed such that it allows at least one specific wavelength of light to pass through, while wavelengths outside of the specific wavelength are filtered out. For this purpose, one of the functional layers of the membrane or matrix is designed as a layer with a filtering function.

In an embodiment of the optochemical sensor the light source and detector unit are arranged directly at the region of the optical component facing away from the medium. The measuring radiation or light is radiated directly toward the optical component, or the detector unit receives the light directly from the optical component. In this context, "direct" means without an intermediate optical waveguide.

An alternative embodiment of the optochemical sensor provides for at least one optical waveguide by means of which the light is guided from the light source to the region of the optical component facing away from the medium, and from the region of the optical component facing away from the medium to the detector unit.

Another embodiment of the sensor according to the present disclosure with the sensor cap provides that the optical waveguide be designed as a dimensionally stable, rod-shaped component on which the optical component is formed on the end region facing the medium. The optical waveguide and optical component accordingly form an integral unit.

The optical component may consist of a solid such as glass. In some of the embodiments described in this application, the optical component can, however, be made from at least one elastic material. Furthermore, the optical component can be constructed from a solid material and an elastic material. Depending upon the sensor design, the region of the optical component that is in contact with the sleeve-shaped component, for example, consists of an elastic material, whereas the rest is made of a solid.

BRIEF DESCRIPTION OF THE DRAWINGS

The present disclosure is explained in greater detail with reference to the following figures. Illustrated are.

DETAILED DESCRIPTION

FIG. 1 shows a longitudinal section of an optochemical sensor cap 2 known from the prior art. FIG. 1A shows an enlargement of the section designated A from FIG. 1. The sensor cap 2 consists of a cylindrical housing, frequently also termed a spot housing, that consists of a sleeve-shaped outer component 6 and a plug-in component 5. The components 5, 6, 7 are connected to each other in a region of the sensor shaft by means of a threaded joint 35.

The end region of the cylindrical housing facing the medium 3 is closed by a matrix 11 for determining the analyte 4. The analytes 4 to be determined or monitored are any ions or gases that are present in the medium 3. The analyte-sensitive matrix 11 preferably consists of several functional layers. One of the functional layers 12 contains the analyte-sensitive substance.

In the known solution, a round, flat, transparent glass substrate is used as the optical component 7 or optical part, with a surface facing the media 3 on which the analyte-sensitive matrix 11 is applied. The end region facing the medium 3 of the sleeve-shaped outer component 6 has an annular recess 38 in which an O-ring 16 is inserted as a seal. By means of the O-ring 16, the sleeve-shaped outer component 6 in the connecting region 10 is sealed axially and gap-free against the analyte-sensitive matrix 11 or membrane.

The known design satisfies all required sensitive, hygienic, and load-specific requirements that are imposed upon an optochemical sensor or an optochemical sensor cap. In certain applications, the connection in the edge region of the membrane 11 recessed towards the inside is, however, disadvantageous. If the sensor is installed substantially vertically in a container or pipeline, there is a danger of gas bubbles collecting on the analyte-sensitive membrane 11, which normally causes measuring errors in determining the analyte 4. Of course, this effect is particularly problematic for an oxygen sensor.

In addition, sensors have been disclosed with a slightly convex deformation of the sensitive component, which is also termed a spot. The seal is provided, on the one hand, by gluing the coated glass substrate 7 to the outer component 6 (also termed the spot sleeve) and, on the other hand, by the spot sleeve 6 directly pressing the sensitive matrix 11 or membrane. The two known seal variants do not satisfy the demanding hygienic requirements or prevent bubbles from adhering to the analyte-sensitive membrane 11 as effectively as the present solution according to the present disclosure.

Figure 2:
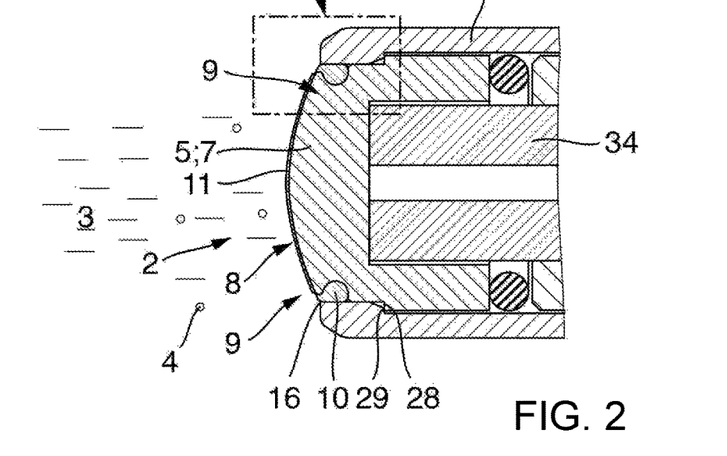
FIG. 2 shows a longitudinal section of a first variant of the sensor cap according to the present disclosure.
Figure 2A:
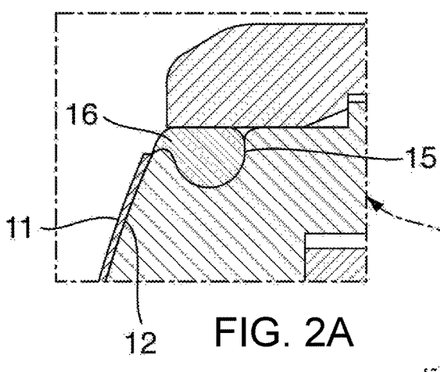
FIG. 2A shows an enlargement of the section designated A from FIG. 2.

FIG. 2 shows a longitudinal section of a first variant of the sensor cap 2 according to the present disclosure. FIG. 2A shows an enlargement of the section designated A from FIG. 2. In this variant, the optical component 7 is simultaneously designed as a plug-in component 5. In terms of production engineering, this solution is particularly useful, since the plug-in component 5 and optical component 7 form an integral unit. The optical component 5 is preferably made of a transparent plastic or, alternatively, of quartz glass. To satisfy the optical requirements, it is also sufficient when at least a portion of the surface region 8 that is shaped convexly or shaped to optimize flow of the optical component 7 consists of a material that is transparent to the measuring radiation of the light source, which light source is not shown separately in FIG. 1.

The analyte-sensitive matrix 11 is applied directly to the surface region 8 facing the medium 3. This preferably consists of a multilayer system with different functional layers 12, 13, 14. Two examples of a multilayer system are described further in FIGS. 4 and 5.

Figure 5:
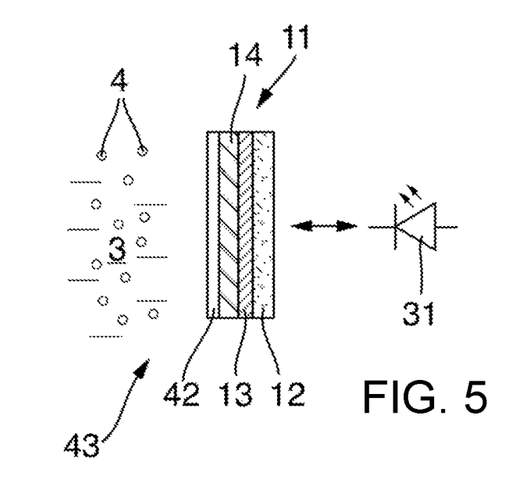
FIG. 5 shows a cross-section of a second variant of an analyte-sensitive membrane, which is used together with the sensor cap according to the present disclosure.

In all the designs of the sensor cap 2 according to the present disclosure, the multilayer system is also applied using a spray coating method, or using another known application method. Either the functional layers 12, 13, 14 of the matrix 11 are applied directly to the surface region 8, or they are applied on a substrate film 41 or a mesh 42 as shown in FIGS. 4 and 5, wherein the membrane 43 formed in this manner is then brought into contact with the surface region 8. The matrix 11 or membrane 43 covers at least a portion of the surface region 8 formed to optimize flow. To ensure a physically and chemically secure bond between the matrix 11 or membrane 43 and the surface region 8, the material of the optical component 7 is strongly adhesive in at least the surface region 8, or it can be adhesively activated by a corresponding surface-activation method. This also applies, in turn, to all of the embodiments of the sensor cap 2 according to the present disclosure described in this application.

The plug-in component 5 corresponds to the optical component 7 in the case depicted. The plug-in component 5 and the sleeve-shaped component 6 are designed such that the connecting region 10 coming into contact with the medium 3 between the plug-in component 5; 7 and the sleeve-shaped outer component 6 lies in the edge region 9 of the convex-shaped surface region 8 of the optical component 7 and is sealed gap-free against the medium 5. For this purpose, the plug-in component 5 or optical component 7 has an annular recess 15 for accommodating a sealing ring 16 in the edge region 9 of the convex-shaped surface region 8. Of course, other seals, such as molded seals, can also be used. The annular recess 15 is thus introduced directly into the optical component. The sealing ring 16 seals the connecting region 10 in a radial and gap-free manner. In the context of the solution according to the present disclosure, "gap-free" means that, in the connecting region 10 coming into contact with the medium, no cavities arise in which medium particles can accumulate in such a way that they cannot be eliminated using cleaning processes common in automation engineering.

At the overlapping region of the plug-component 5 and sleeve-shaped outer component 6 in the region of the sensor shaft, corresponding stop edges 28, 29 are provided for the purpose of a specific axial positioning of the plug-in component 5 or optical component 7 in the sleeve-shaped outer component 6. Preferably, the two components 5, 6 are connected to each other by means of a press fit.

In the depicted embodiment, mechanical stress on the sensitive matrix 11 is prevented, since there is no contact between the sealing ring 16 and the analyte-sensitive matrix 11 or membrane. The optical component 7 is coupled to one or more optical waveguides 34. Alternatively, the light source 31 and detector unit 32 can also interact directly with the optical component 7, i.e., without interposing at least one optical waveguide 34. Given an appropriate selection of the material and an appropriate design, the optical component 7 can also assume additional functions. Accordingly, the optical component 7 can also be designed as a one-sided or two-sided filter element for diverse light spectra, as a prismatic element for beam deflection and/or beam division, or as a one-sided, two-sided, full-reflecting, or half-reflecting element. This possibility applies as well to all of the solutions according to the present disclosure described in this application.

A suitable material for the optical component 7 is, for example, transparent to a selected wavelength range. It is dimensionally stable under heat, gas-tight, non- or only slightly swelling (water absorbent), and/or chemically resistant. Quartz glass, for example, has all of these properties; however, there are also suitable plastics that fully satisfy the aforementioned properties.

To prevent an axial shift of the plug-in component 5 or optical component, e.g., due to pressure from the medium, the plug-in component 5 is arrested by a fixed part located in the region of the center shaft. In the depicted case, this fixedly installable part is the sleeve of an optical waveguide 34.

A preferred embodiment of the variant described in FIG. 2, which is not depicted separately, provides that the optical component 7 be designed elastically, at least in the edge region 9 of the surface region 8. In this case, the sealing ring 16 can be omitted. The gap-free seal can be achieved by the clamp connection between the suitably designed edge region of the sleeve-shaped outer component 6 and the elastically designed edge region 9 of the surface region 8 of the optical component 7.

The primary advantage of first variant of the sensor cap 2 according to the present disclosure is that only a single part is used as the plug-in component 5, which part assumes a variety of different mechanical and optical functions, due to the corresponding design. These functions are, in particular:

Support element for the analyte-sensitive matrix;
Avoiding bubble formation on the matrix 11 due to the convex or flow-optimized shape of the optical component 7;
Design of the optical component 7 as a mechanical fastening element for fastening the plug-in component 5; 7 in the sleeve-shaped outer component 6;
Optical connection element between the optical waveguide 34 and sensitive matrix 11; and
Support of the sealing ring 16 for the gap-free seal.

Other advantageous embodiments of the optical component 7 have already been described in conjunction with the first variant of the sensor cap 2 according to the present disclosure.

Further advantages are:
There is only one potentially exchangeable sealing ring 16 that comes into contact with the medium 3;
The connection satisfies the demanding hygienic requirements, e.g., for use in the food industry or pharmaceutical industry;
The analyte-sensitive matrix 11 has a flow-optimized, convex or flat shape;
The analyte-sensitive matrix 11 is not subject to a mechanical load;
The spot sleeve or sleeve-shaped outer component is reusable; and Installation or exchanging the spot is easy to perform.

A majority of the aforementioned advantages also apply to the solutions described below. Which these are is easily discernible by a professionally qualified person in each individual case.

Figure 3:
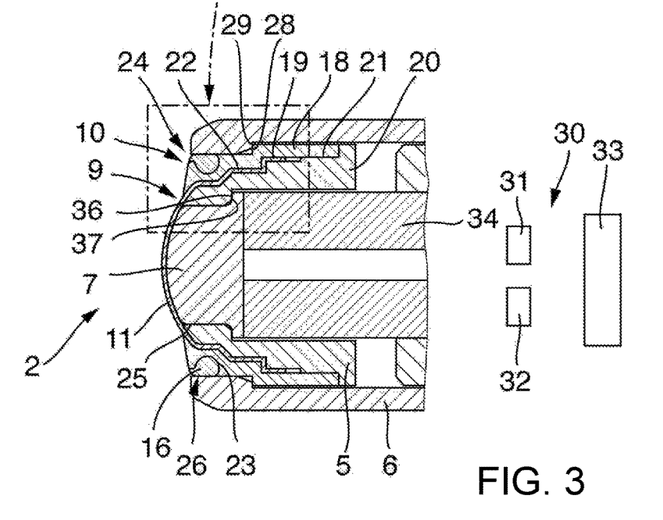
FIG. 3 shows a longitudinal section of a second variant of the sensor cap according to the present disclosure as well as a schematic view of an optochemical sensor including the sensor cap.
Figure 3A:
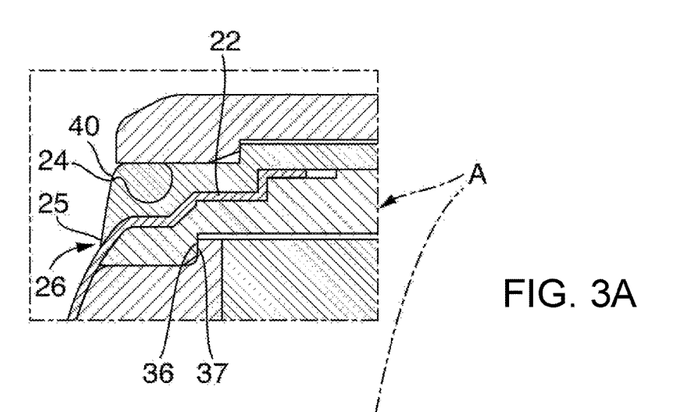
FIG. 3A shows an enlargement of the section designated A from FIG. 3.

FIG. 3 shows a longitudinal section of a second variant of the sensor cap 2 according to the present disclosure. FIG. 3A shows an enlargement of the section designated A from FIG. 3. Whereas the optical component 7 was simultaneously designed as a plug-in component 5 in the aforementioned embodiments, these two functions are separated in the embodiment shown in FIG. 3.

The mechanical fastening of the plug-in component 5 in the sleeve-shaped outer component 6 is achieved by an outer ring 18 and an inner ring 20, wherein the outer component 6 has an inner contour 19 that corresponds to the outer contour 21 of the inner ring 20. The optical component 7 is connected to the plug-in component 5 by means of corresponding stop edges. These are the stop edges 36, 37 on the optical component 7 and inner ring 20. In the depicted case, axial fixation in the direction facing away from the medium 3 is accomplished, on the other hand, by the sleeve of the optical waveguide 34. A professionally qualified person is familiar with other fastening options.

The end region of the inner ring 20 facing the medium 3 that lies against the convex-shaped surface region 8 of the optical component 7 is shaped such that there is a smooth transition between the two components. The curvature of the surface region 8 accordingly continues in the end region of the inner ring 20 facing the medium 3.

The analyte-sensitive membrane 11 is preferably designed such that its edge region projects beyond the convex-shaped surface region 8 and the adjoining end region of the inner ring 20 facing the medium 3. The projecting edge region of the analyte-sensitive membrane 11 is clamped between the outer ring 18 and the inner ring 20 when the two rings 18, 20 are pressed together. Of course, it is sufficient when the individual functional layers 12, 13, 14 are applied only in the region of the flow-optimized, shaped surface region 8 of the optical component 7.

The inner edge 25 of the end region of the outer ring 18 facing the medium 3 is shaped so that it forms a gap-free connection 10 together with the flexibly designed membrane 11. The connecting region 10 preferably lies to the outside of the analyte-sensitive coating of the membrane 11. A mechanical load on the membrane 11 is avoided in the region of the analyte-sensitive coating. Since the membrane 11 is pressed between the outer ring 18 and inner ring 20, preferably irreversibly, the membrane 11 simultaneously fulfills the function of a hygienic seal.

At the end region facing the medium 3, the outer ring 18 possesses an annular recess 23 in the region of the outer edge 24 for accommodating a sealing ring 16. The annular recess 15 and sealing ring 16 are arranged and designed so that the gap-free connection 10 is produced between the plug-in component 5—here, in particular, the outer edge of the outer ring 18—and the sleeve-shaped outer component 6. In this embodiment, the gap-free hygienic connection 10 between the plug-in component 5 and sleeve-shaped outer component 6 is accordingly at a radial distance from the edge region 9 of the convex-shaped surface region 8 of the optical component 7.

The optical link of the optical waveguide 34 to the sensitive membrane 11 or matrix is accomplished by the optical component 7, which is designed as either a solid molded part or an elastic molded part, depending upon the variant of the sensor cap 2 according to the present disclosure. Together with the analyte-sensitive membrane 11 and the plug-in component 5 composed of the inner ring 20 and outer ring 18, the optical component 7 provides a secure connection that can be exchanged as needed.

As already mentioned in the context of the description of the first variant of the sensor cap 2 according to the present disclosure, the optical component 7 can assume a variety of functions, given a corresponding design. Beyond the requirement of high permeability to light within the desired spectral range, the optical component 7 can also assume shaping functions. The shape, of whatever nature, of the membrane 11 is provided by the geometry of the optical component 7. Additional options have already been described in conjunction with the first variant of the sensor cap 2 according to the present disclosure and can, of course, also be used for this and the embodiments of the present disclosure described below.

The advantages of the second variant of the sensor cap 2 according to the present disclosure are, in particular:

- The surface region 8 of the optical component 7 facing the medium 3 is separated from the medium 3 by means of the analyte-sensitive matrix 11. Any matrix post-treatment methods such as cleaning processes therefore stress only the analyte-sensitive matrix 11 or membrane, but not, however, the optical component 7.
- There is only one, potentially exchangeable, sealing ring 16 that comes into contact with the medium 3.
- The connection is between the plug-in component 5 and outer component 6, which satisfies the demanding hygienic requirements for, for example, use in the food industry or pharmaceutical industry.
- The analyte-sensitive matrix 11 has a flow-optimized, convex or flat shape.
- In the analyte-sensitive surface region 8, the matrix is mechanically unstressed.
- The spot sleeve or the sleeve-shaped outer component 6 is reusable.
- Installation or exchanging the spot is easy to perform.
- The optical component 7 with the flow-optimized shape has a simple design.

In this case as well, the following holds true: A majority of the aforementioned advantages also apply to other variants of the solution according to the present disclosure. Which these are is easily discernible by a professionally qualified person in each individual case.

FIG. 4 shows a cross-section of a first variant of an analyte-sensitive membrane 11 which is used together with the sensor cap 2 according to the present disclosure. A film 41 that is preferably impermeable to the medium and the analyte serves as the support element to which is applied the matrix 11 that consists of three functional layers 12, 13, 14 and forms the layer structure. One of the functional layers 12, 13, 14 contains the analyte-sensitive substance. This provides a selective analyte permeability and, when appropriately excited, emits a luminescence or fluorescence or phosphorescence signal at a specific wavelength and/or an analyte-specific phase angle, or it absorbs light.

An additional functional layer ensures that the incoming interference radiation from the surroundings is at least partially absorbed. Another layer ensures, for example, physical and/or chemical stability. Depending upon the application, the composition of the functional layers can vary.

FIG. 5 shows a cross-section of a second variant of a membrane 43, which is used together with the sensor cap 2 according to the present disclosure. The matrix 11 is applied to a mesh 42 that is permeable to the analyte 4, such as a metal mesh, as a support element. This embodiment of the membrane 43 is distinguished by a high flexibility, which, in particular, simplifies its connection to the optical component 7. With regard to the construction of the layer structure of the matrix 11, reference is made to the exemplary description of FIG. 4. It goes without saying that the layer construction of the matrix 11 can be designed to be very flexible.

Figure 6A:
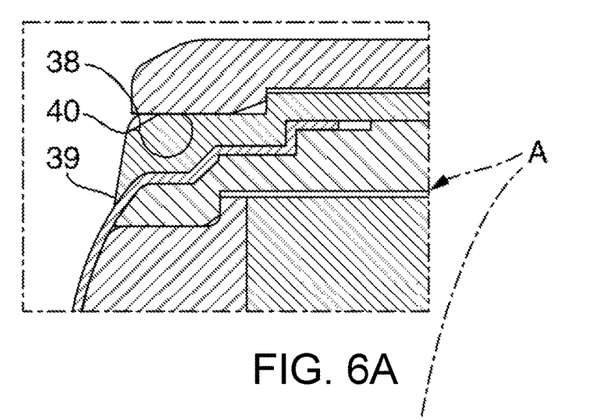
FIG. 6A shows an enlargement of the section designated A from FIG. 6.

FIG. 6 shows a longitudinal section of a third variant of the sensor cap 2 according to the present disclosure, which has only a structural modification with respect to the second variant shown in FIG. 3. FIG. 6A shows an enlargement of the section designated A from FIG. 6. In this variant, the inner ring 20 that is described in FIG. 4 and forms an element of the plug-in component 5 is an integral part of the optical component 7. Accordingly, the optical component 7 assumes shape-forming and structurally-sealing, as well as optical, tasks.

Figure 7:
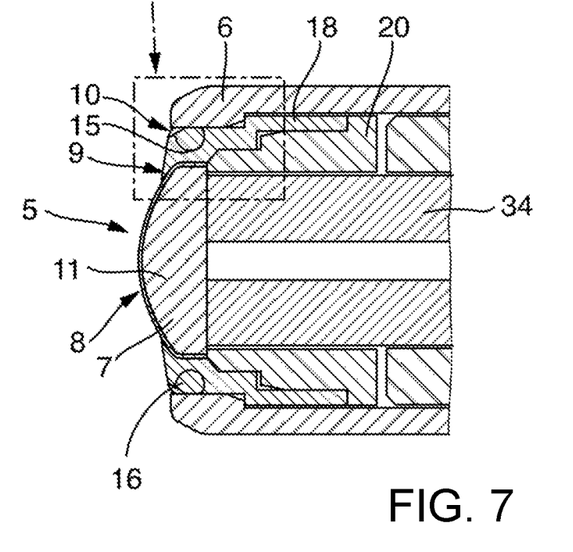
FIG. 7 shows a longitudinal section of a fourth variant of the sensor cap according to the present disclosure.
Figure 7A:
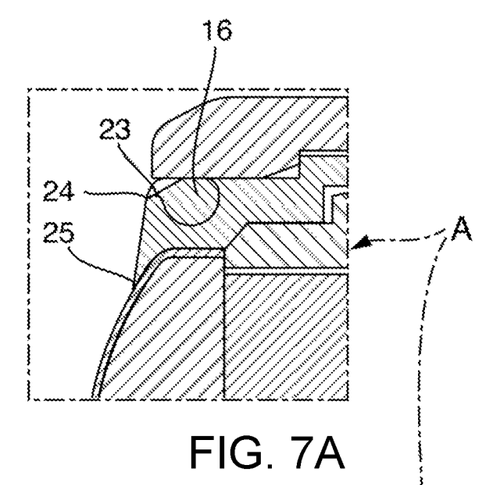
FIG. 7A shows an enlargement of the section designated A from FIG. 7.

FIG. 7 shows a longitudinal section of a fourth variant of the sensor cap 2 according to the present disclosure. FIG. 7A, on the other hand, shows an enlargement of the section designated A from FIG. 7.

The fourth variant is very similar to the second variant of the sensor cap 2 according to the present disclosure shown in FIG. 3; however, it differs from the second variant in that the sensitive membrane 11 is not fixed between the outer ring 18 and inner ring 20. In the depicted case, the inner ring 20 is designed as a press ring. The press ring fixes the optical component 7 in an axial direction. The contact pressure of the press ring 20 is, for example, provided by means of screwing to the outer ring 18 or by pressing.

In this variant, the optical component 7 is again designed very simply. The gap-free connection 10 to the optical component 7 is achieved, as in the variant shown in FIG. 3, by the specific shape of the inner edge 25 of the outer ring 18. Either the corresponding edge region 9 of the elastically designed matrix 11 is used as a seal, or the optical component 7 is designed to be flexible, at least in the corresponding contact region 26, and assumes the sealing function.

The gap-free connection 10 between the outer ring 18 and sleeve-shaped outer component 6 or spot sleeve is provided by the sealing ring 16 that is positioned in the annular recess 23 in the outer edge 24 of the outer ring 18. See the description of FIG. 3 for further details.

What is claimed is:

1. A sensor cap for an optochemical sensor, comprising:
   a substantially cylindrical plug-in component integral with an optical component having a surface region shaped for optimal flow, the optical component disposed in an end region of the plug-in component facing a medium, the optical component having a matrix on the surface region, the matrix having an analyte-sensitive functional layer; and
   a sleeve-shaped outer component,
   wherein near the surface region, the optical component is embodied at least partially of a material transparent to measuring radiation;
   wherein the plug-in component and the outer component are configured such that a connecting region coming into contact with the medium is formed between the plug-in component and the outer component in an edge region of the surface region and is sealed without a gap facing the medium; and
   wherein the plug-in component or the optical component includes an annular recess for receiving a sealing ring in the edge region of the surface region, and the recess and the sealing ring are configured such that the connecting region is sealed gap-free against the medium.

2. The sensor cap according to claim 1, wherein the matrix is a multilayer system having at least two functional layers, and one of the functional layers includes an analyte-sensitive substance.

3. The sensor cap according to claim 1, the optical component further having a membrane disposed on the surface region, the membrane including the matrix disposed on or in a substrate layer, through which an analyte can diffuse or which blocks an analyte.

4. A sensor cap for an optochemical sensor, comprising:
a substantially cylindrical plug-in component having an optical component having a surface region shaped for optimal flow, the optical component disposed in an end region of the plug-in component facing a medium, the optical component having a matrix on the surface region, the matrix having an analyte-sensitive functional layer; and
a sleeve-shaped outer component,
wherein near the surface region, the optical component is embodied at least partially of a material transparent to measuring radiation,
wherein the plug-in component and the outer component are configured such that a connecting region coming into contact with the medium is formed between the plug-in component and the outer component in an edge region of the surface region or is formed at a radial distance from the edge region of the surface region and is sealed without a gap facing the medium,
the optical component further having a membrane disposed on the surface region, the membrane including the matrix disposed on or in a substrate layer, through which an analyte can diffuse or which blocks an analyte,
wherein the plug-in component is configured as a single part and the matrix or the membrane is flexible and serves as a means of gap-free sealing between the plug-in component and the outer component, and
the plug-in component further having an outer ring having an inner contour and an inner ring having an outer contour corresponding to the inner contour, the outer ring and the inner ring disposed in at least a portion of the axial region where the plug-in component and outer component overlap, wherein in the edge region of the surface region the optical component is connected to the inner ring.

5. The sensor cap according to claim 4, wherein the membrane is dimensioned to be larger than the surface region shaped to optimize flow of the optical component, and the edge region of the membrane projecting beyond the surface region is fixed between the inner ring and outer ring of the plug-in component.

6. The sensor cap according to claim 4, wherein the inner ring with the outer contour is an integral part of the plug-in component.

7. The sensor cap according to claim 4, the outer ring further having an annular recess for accommodating a sealing ring, the annular recess disposed in an end region of the outer ring facing the medium, wherein the recess and a sealing ring are configured such that the connecting region is sealed gap-free against the medium.

8. The sensor cap according to claim 4, wherein the inner contour of the outer ring facing toward the surface region is configured to form a gap-free, annular contact region with the matrix or the membrane.

9. The sensor cap according to claim 4, wherein the inner contour of the outer ring and the outer contour of the inner ring have corresponding helical threads.

10. The sensor cap according to claim 1, wherein corresponding stop edges are provided on an inner surface of the outer component and an outer surface of the plug-in component that limit the position of the plug-in component and outer component in an axial direction.

11. The sensor cap according to claim 1, wherein the matrix is disposed on or in a mesh through which an analyte can diffuse, or on or in a transparent substrate layer that blocks an analyte.

12. An optochemical sensor for determining or monitoring at least one analyte present in a medium, comprising:
a sensor cap comprising:
a substantially cylindrical plug-in component integral with an optical component having a surface region shaped for optimal flow, the optical component disposed in an end region of the plug-in component facing a medium, the optical component having a matrix on the surface region, the matrix having an analyte-sensitive functional layer; and
a sleeve-shaped outer component, wherein near the surface region, the optical component is embodied at least partially of a material transparent to measuring radiation, and wherein the plug-in component and the outer component are configured such that a connecting region coming into contact with the medium is between the plug-in component and the outer component in an edge region of the surface region and is sealed without a gap facing the medium;
an electronic component having a light source, a detection unit, and a control/evaluation unit; and
wherein the plug-in component or the optical component includes an annular recess for receiving a sealing ring in the edge region of the surface region, and the recess and the sealing ring are configured such that the connecting region is sealed gap-free against the medium.

13. The optochemical sensor according to claim 12, wherein the optical component is configured to allow at least one specific wavelength of light to pass through and to filter out wavelengths outside of the specific wavelength.

14. The optochemical sensor according to claim 12, wherein the light source and the detector unit are arranged at a region of the optical component facing away from the medium.

15. The optochemical sensor according to claim 12, further comprising at least one optical waveguide configured to guide light from the light source to a region of the optical component facing away from the medium and from the region of the optical component facing away from the medium to the detection unit.

16. The optochemical sensor according to claim 15, wherein the optical waveguide is a dimensionally stable, rod-shaped component on which the optical component is formed on an end region facing the medium.

17. The optochemical sensor according to claim 12, wherein the optical component is embodied at least partially of an elastic material.

18. The optochemical sensor according to claim 12, wherein the matrix is disposed on or in a mesh through which an analyte can diffuse, or on or in a transparent substrate layer that blocks an analyte.

* * * * *